US006884615B2

(12) United States Patent

Suzuki et al.

(10) Patent No.: US 6,884,615 B2
(45) Date of Patent: *Apr. 26, 2005

(54) MICROPLATE

(75) Inventors: Hideyuki Suzuki, Mobara (JP); Yoshikatu Sekine, Mobara (JP); Hisao Kuramoto, Mobara (JP); Maki Kaneko, Chiba (JP)

(73) Assignee: Futaba Corporation, Mobara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/614,963

(22) Filed: Jul. 8, 2003

(65) Prior Publication Data

US 2004/0009101 A1 Jan. 15, 2004

(30) Foreign Application Priority Data

Jul. 9, 2002 (JP) ....................................... 2002-200538

(51) Int. Cl.$^{7}$ ................................................ C12M 1/34

(52) U.S. Cl. ........................ 435/288.4; 422/57; 422/58; 422/99; 422/102; 436/809

(58) Field of Search ............................. 422/57, 58, 99, 422/102; 435/288.4; 436/809

(56) References Cited

U.S. PATENT DOCUMENTS 3,356,462 A 12/1967 Cooke et al.
4,468,371 A * 8/1984 Chen et al. ................. 422/102
4,510,119 A * 4/1985 Hevey ......................... 422/71
4,735,778 A * 4/1988 Maruyama et al. ......... 422/102
4,761,378 A * 8/1988 Godsey ................... 435/288.4
4,770,856 A * 9/1988 Uthemann et al. .......... 422/104
4,891,321 A * 1/1990 Hubscher ..................... 422/57
4,919,894 A * 4/1990 Daniel ........................ 422/104
4,948,442 A * 8/1990 Manns ...................... 156/73.1
5,084,246 A * 1/1992 Lyman et al. ............... 422/101
5,110,556 A * 5/1992 Lyman et al. ............... 422/101
5,487,872 A * 1/1996 Hafeman et al. ........... 422/102
5,603,899 A * 2/1997 Franciskovich et al. .... 422/100
5,766,554 A * 6/1998 Liu ............................ 422/102
6,096,562 A * 8/2000 Bunn et al. ................. 436/518
6,258,326 B1 * 7/2001 Modlin ....................... 422/102
6,383,820 B1 * 5/2002 Bunn et al. ................. 436/518

FOREIGN PATENT DOCUMENTS

EP 1053790 A2 11/2000
JP 56115953 9/1981
JP 513399 1/1993
JP 08114596 5/1996

* cited by examiner

*Primary Examiner*—Christopher L. Chin
(74) *Attorney, Agent, or Firm*—Quarles & Brady LLP

(57) ABSTRACT

A microplate having a base and wells is disclosed. The base has mark parts at least on one edge thereof. Each mark part is defined by notches cut in the edge of the base. The wells are provided in the base and arranged in rows and columns. The mark parts can be used as indicia for identifying not only the microplate but also the wells so that the microplate and the wells can be easily identified without writing numerals or marks on the edges of the base with a felt pen or the like.

3 Claims, 6 Drawing Sheets

1
3
3a
5
5(a)
5(b)
5(c)
6
A
B
C
D
E
F
G
H
1
2
3
4
5
6
7
8
9
10
11
12

MICROPLATE

BACKGROUND OF THE INVENTION

1. Field of the Invention

The present invention relates to a microplate for use in examining samples in the course of clinical examination, DNA analysis and the like.

2. Description of the Related Art

Microplates are vessels widely used in clinical examination, DNA analysis and the like. A microplate has a well, in which a small amount of a liquid sample or a liquid reagent may be contained. There is known such a method that a liquid sample contained in the well of a microplate is subjected to a reaction such as heat cycle or centrifugal separation, a light beam is applied to the liquid sample, and the intensity of the light passing through the sample is measured to determine the results of the reaction. In this method, the composition of the sample and the content of each component thereof can be determined. Inasmuch as a very small amount of a sample or a reagent is required in this method, the method is widely employed to examine blood or urine in diagnosis, to perform DNA analysis, and other clinical examination.

In such a method, it is necessary to divide the same sample into small portions so as to react each of the divided samples with various reagents, respectively, to perform various items of examination. Alternatively, various samples are reacted with the same reagent to conduct one item of examination. To carry out such examination with high efficiency, microplates of the type shown in FIGS. 6A and 6B have been conventionaly used.

FIG. 6A is a side view of a conventional microplate 1, and FIG. 6B is a plan view thereof. The microplate 1 comprises wells 2 and a base 3. The base 3 is substantially rectangular plate. The wells 2 are hollow cylinders, each shaped like a test tube and opening at the top. Each well 2 has an inner wall indicated by the broken line, as shown in FIG. 6A (side view), and can contain a sample. The base 3 has a number of openings that are arranged at regular intervals, in rows and columns. The wells 2 are formed integral with the base 3, each fitted at the bottom in one opening, thus forming the microplate illustrated in FIGS. 6A and 6B. Liquid samples or liquid reagents are dripped into the wells 2 by an automatic distributing apparatus. After the sample or reagent in each cell undergoes a prescribed reaction, it is analyzed by using an optical means.

The any adjacent cells of the same row or the same column are spaced apart by 9 mm. The microplate 1 shown in FIG. 6B has 96 wells 2 (arranged in 8 rows and 12 columns) or 24 wells 2 (arranged in 3 rows and 8 columns) as in most practical cases. Each well 2 has a rim 4 at the upper end. The rim 4 is an annular structure that protrudes a little from the base 3. An adhesive film may be adhered to the rim 4 to prevent evaporation of the sample or cross-contamination of the sample with the sample in the adjacent well 2, which may occur during the analysis of the sample. As shown in the side view (FIG. 6A), the lower end portion of each well 2 is conical, closed at the distal end. Alternatively, it may be cylindrical, having a flat and closed distal end, to serve a specific purpose. The base 3 of the microplate 1 may have side walls that project downwards from the four edges, as is disclosed in Jpn. Pat. Appln. Laid-Open Publication No. 56-115953. The microplate 1 is a molding made of transparent synthetic resin, as described also in Jpn. Pat. Appln. Lain-Open Publication No. 56-115953.

The analysis using the microplates 1 is performed on various samples contained in the wells 2 of the microplate 1. Usually, a plurality of microplates 1 are used, subjecting the samples contained in them to various processes, such as heat cycle and centrifugal separation, which are carried out one after another. Since the samples held in one microplate 1 are different from those held in another microplate 1, it is important to identify any microplate 1 easily. To this end, serial numbers or ID marks are written on the bases 3 of the microplates 1 with felt pens or the like.

It is equally important to identify the sample contained in each well 2 of any microplate. Numbers are therefore printed on a long edge of the microplate 1, indicating the columns of wells 2, and letters a short edge of the microplate 1 to indicate the rows of wells 2, as is illustrated in FIG. 6B. Such a method of identifying the samples is disclosed in Jpn. UM. Appln. Publication No. 5-13399.

As described above, a number or mark is written with felt pens on the base 3 of each microplate 1 to identify each microplate 1 and to identify the wells 2 of the microplate 1. However, the number or mark is liable to erase when the microplate 1 is exposed heat, vapor or organic solvent or accessed to by a person or any instrument during the processes of analyzing the samples contained in the wells 2. If this happens, it will be difficult to identify the microplate 1 and to identify any well 2 with its position on the microplate 1. Most microplates 1 are made of polypropylene resin, because this material excels in heat resistance and for some other reasons. Felt-pen ink can hardly firmly stick to anything made of polypropylene. Therefore, the number or mark written in the ink is easily rubbed off as the rubber-gloved hands touch the base 3 of the microplate 1. In this case, the rubber gloves are stained with the ink. If any person handles the microplate 1 while putting on the ink-stained rubber gloves, the liquid samples may be contaminated. Moreover, when the microplate 1 is exposed to heat, the volatile component of the ink may evaporate, and the number or mark will disappear. The volatile component may be dissolved into the liquid samples, inevitably influencing the results of analysis. Obviously it is troublesome to write the number or mark with felt pens on the base 3 of the microplate 1. If several microplates 1 are stuck one upon another, which often occurs during the analysis, the number or mark written on any microplate 1 laid beneath another can hardly be seen from above. Furthermore, one column number is likely to be taken for another, causing errors in identifying the wells 2, because the column numbers are printed at short intervals on the long edge of the microplate 1.

SUMMARY OF THE INVENTION

The present invention has been made to solve the problems pointed out above. A first object of the invention is to provide a microplate that can be easily distinguished from any other. A second object of the invention is to provide a microplate with which it is easy to identify the wells.

A microplate according to the present invention comprises: a base having mark parts at least on one edge thereof, each mark part being defined by notches cut in the one edge; and a plurality of wells provided in the base and arranged in rows and columns.

In an embodiment of the microplate of the invention, some of the mark parts may be aligned with the rows of wells, respectively, and the remaining mark parts may be aligned with the columns of wells, respectively.

In another embodiment of the microplate of this invention, each of the wells may have a rim at the upper end, and the wells of every other row or every other column are different in color from the base.

DETAILED DESCRIPTION OF THE PREFERRED EMBODIMENTS

Figures 1A, 1B, 1C:
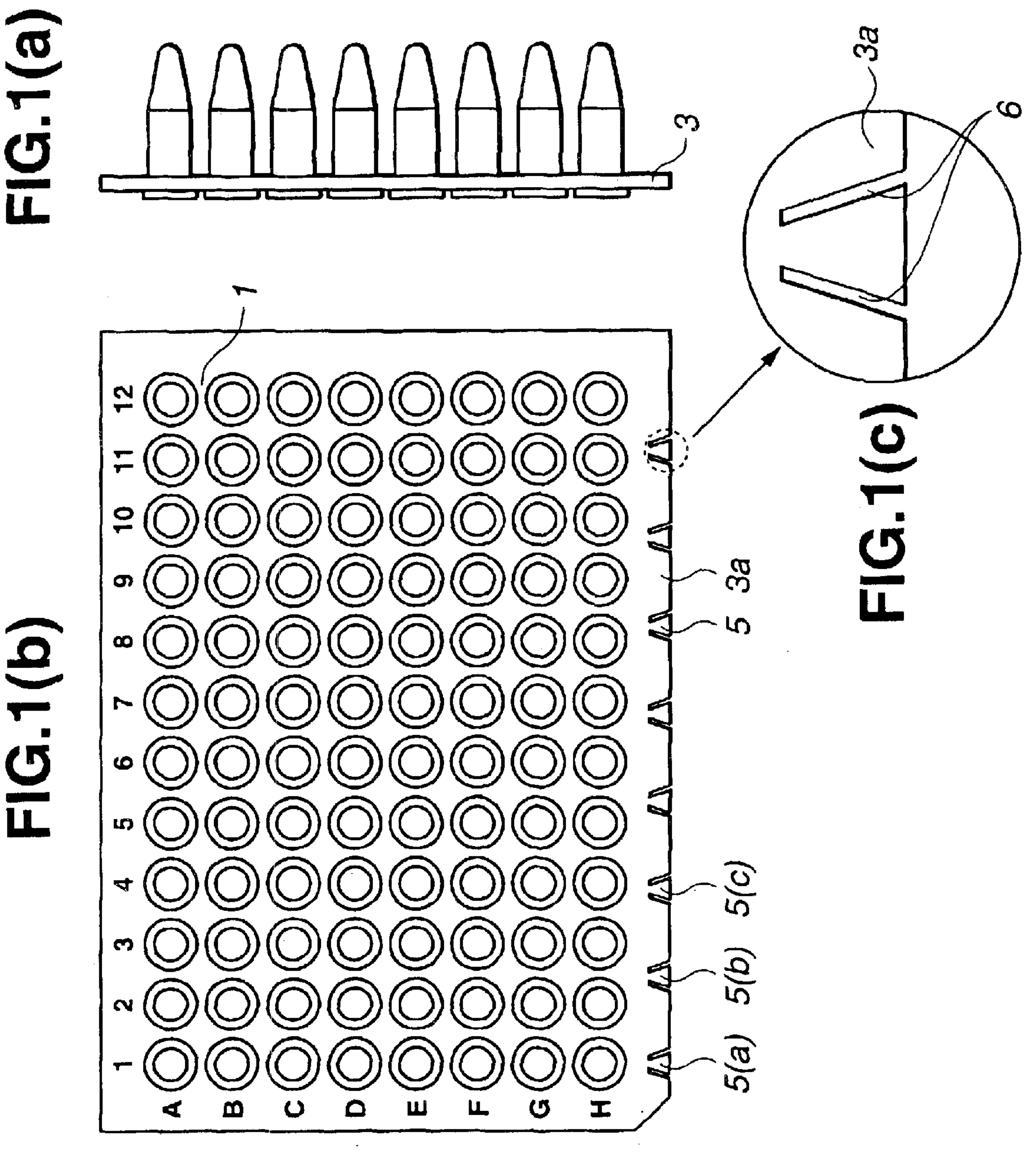
FIG. 1A is a side view of a microplate according to the first embodiment of this invention.
FIG. 1B is a plan view of the microplate.
FIG. 1C is a magnified view of one of the marks provided on a long edge of the microplate.
Figure 6A:
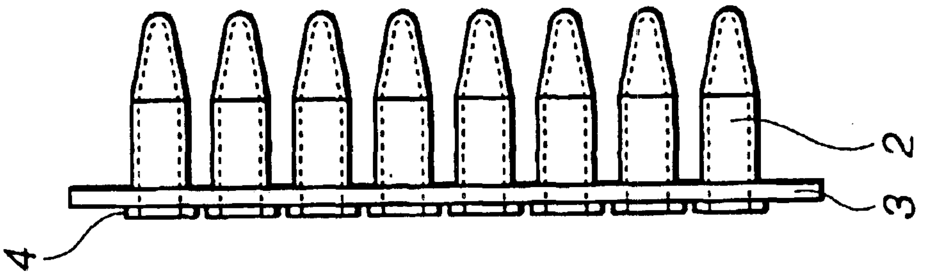
FIG. 6A is a side view of a conventional microplate.
Figure 6B:
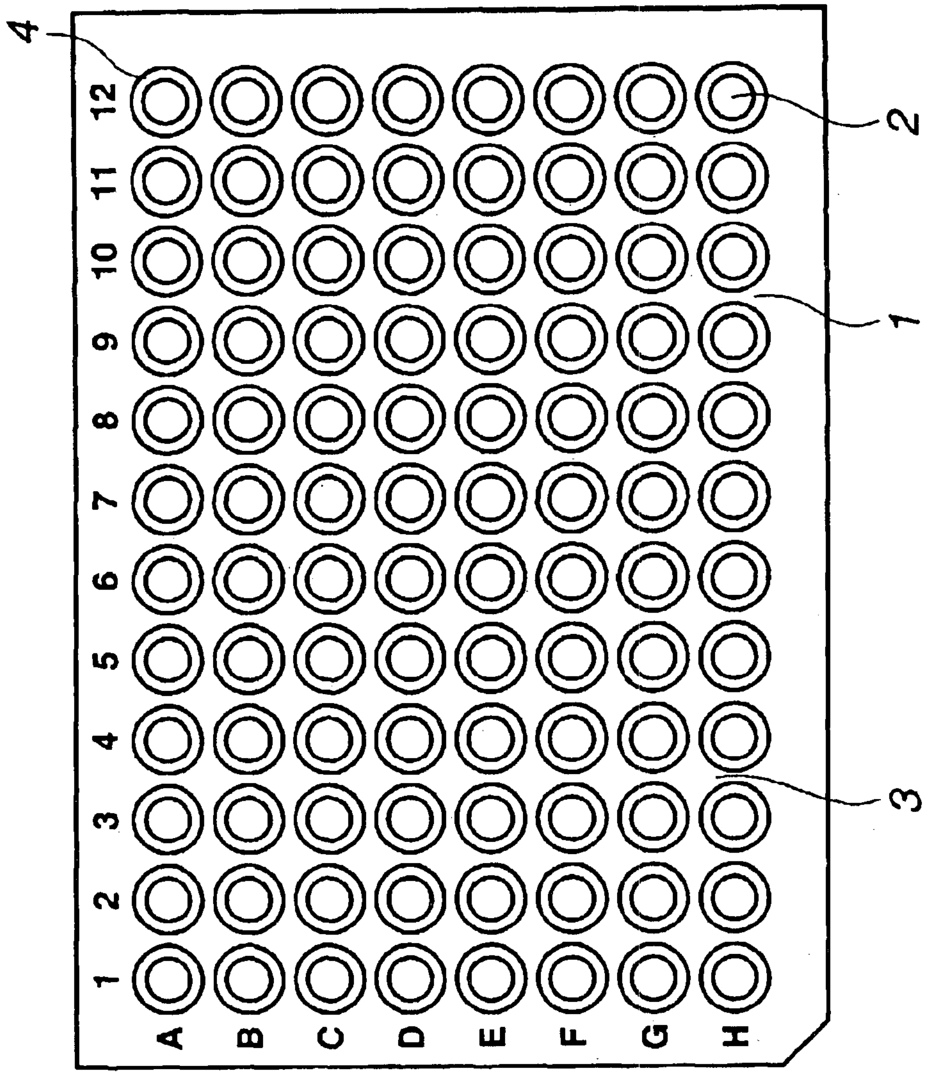
FIG. 6B is a plan view of the conventional microplate.

FIGS. 1A, 1B and 1C show a microplate 1 according to the first embodiment of the present invention. FIG. 1A is a side view of the microplate 1, and FIG. 1B is a plan view thereof. The microplate 1 is identical in basic structure to the conventional one illustrated in FIGS. 6A and 6B. Hence, the components similar or identical to those of the conventional microplate are designated at the same reference numerals and will not be described in detail. As shown in FIG. 1B, the base 3 of the microplate 1 has mark parts 5 that are provided at a long edge 3*a*. FIG. 1C is a magnified view depicting one of the mark parts 5. As shown in FIG. 1C, two elongate notches 6 are cut in each mark part 5. The notches 6 incline such that they are most spaced at the edge of the base 3 and least spaced at a position near the wells. In other words, the distance between the notches 6 gradually decreases from the edge of the base 3 toward the wells. Thus, each mark part 5 is trapezoidal, with its base flush with the edge of the base 3 and its top located close to the wells. The base 3 is 0.9 mm thick. The mark part 5 is 4.0 mm high, 5.0 mm wide at the base, and 0.8 mm at the top. Both notches 6 have a width of 0.5 mm. Note that mark parts 5 are formed at the same time the microplate 1 is made of thermoplastic resin by means of injection molding. The thermoplastic resin is, for example, polypropylene, polystyrene, polycarbonate, polyethylene or the like.

How the microplate 1 of the structure shown in FIGS. 1A to 1C is used will be explained. Liquid samples are dripped into the wells of the microplate 1, respectively. Assume three microplates 1 are used in the same analysis. The mark 5(*a*) (FIG. 1B) of the first microplate is bent to identify the first microplate. Similarly, the mark 5(*b*) (FIG. 1B) of the second microplate is bent to identify the second microplate, and the mark 5(*c*) (FIG. 1B) of the third microplate is bent to identify the third microplate. The marks 5(*a*), 5(*b*) and 5(*c*) can be easily bent with the finger tips, either before or after the samples are dripped into the wells. Alternatively, the marks 5(*a*), 5(*b*) and 5(*c*) may be cut off. In this case, too, it is possible to identify the three microplates 1.

Figure 2:
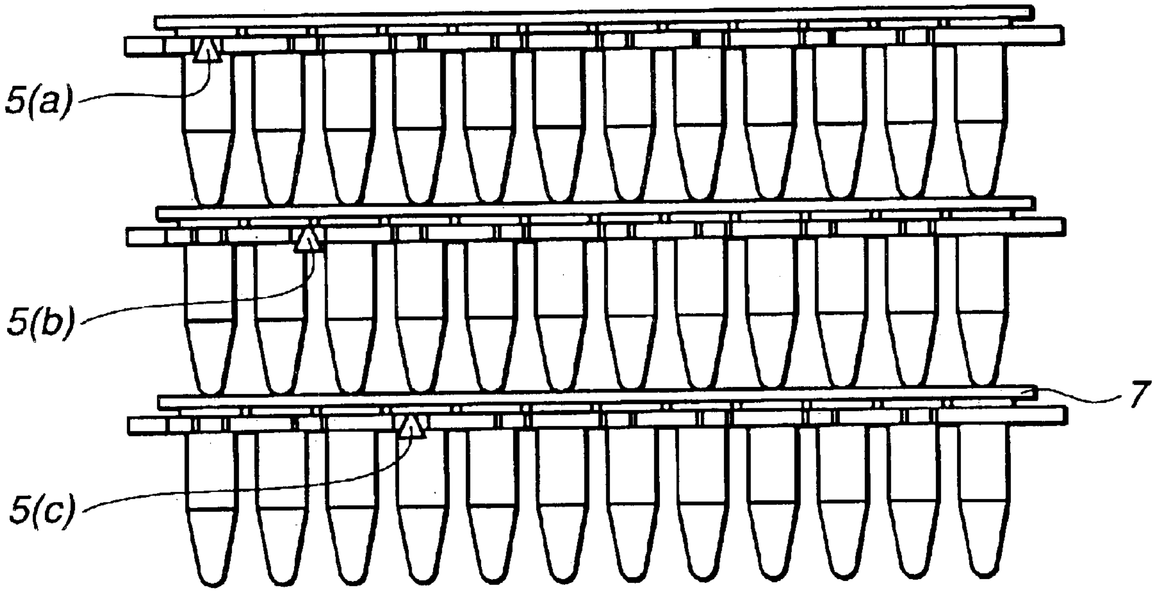
FIG. 2 is a side view showing three microplates of the type shown in FIGS. 1A to 1C, stuck one upon another, each having a cover mounted on it.

FIG. 2 shows the three microplates 1 stacked one upon another. As seen from FIG. 2, the microplates 1 can be distinguished from one another when they are viewed sideways, in accordance with the different positions of the mark parts 5(*a*), 5(*b*) and 5(*c*) bent.

Microplates 1 according to the first embodiment were made for test, using polypropylene. In the test, one of the mark parts 5 of each microplate was bent to identify the microplate. The microplates 1 were then used at temperatures ranging from −80° C. to 125° C. The mark part 5 of every microplate tested remained bent in the original state.

The mark part 5 of the microplate 1 may be cut off. If so, the microplate 1 cannot be identified because the absence of the mark part 5 is a somewhat less conspicuous than a mark part 5 bent when the microplate 1 is viewed from the side. Nonetheless, the absence of the mark part 5 can be well ascertained when the microplate 1 is viewed slantwise.

Figure 3:
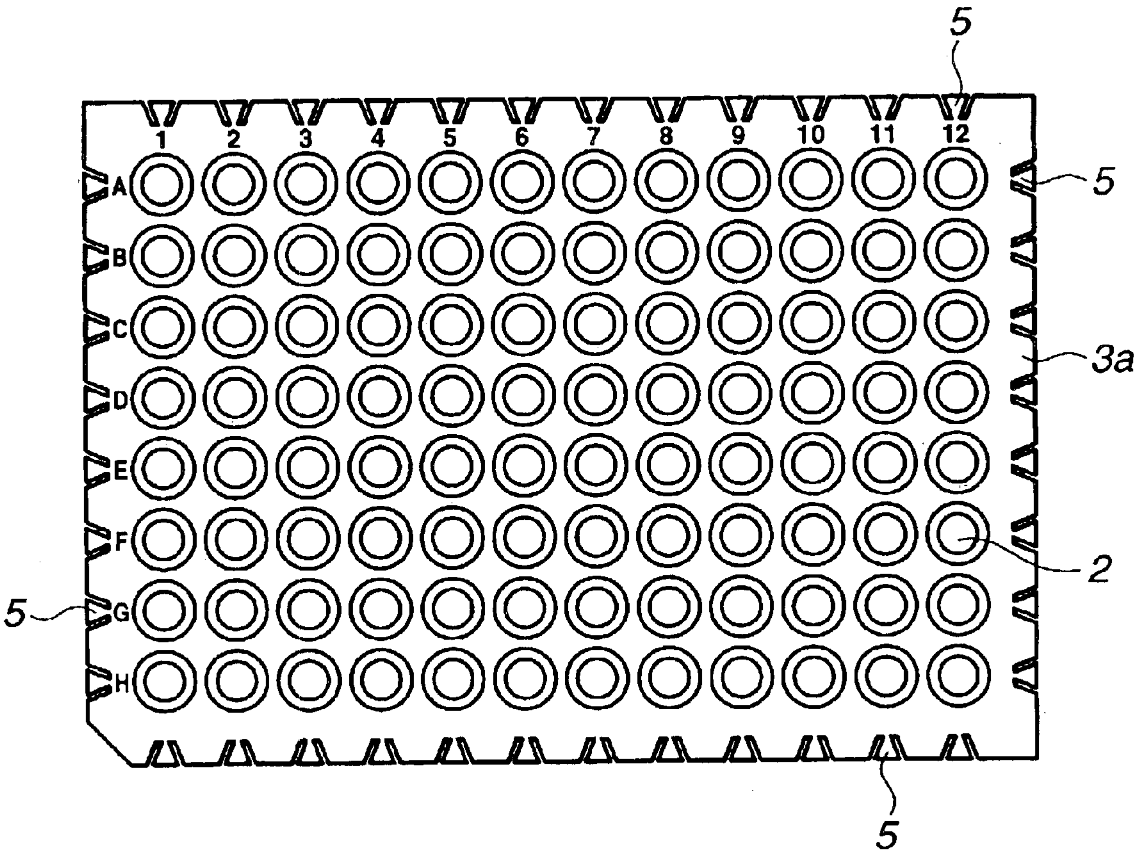
FIG. 3 is a top view of a microplate according to the second embodiment of this invention.

A microplate 1 according to the second embodiment of the invention will be described with reference to FIG. 3. The components similar or identical to those of the first embodiment are designated at the same reference numerals and will not be described in detail. In the second embodiment, the base 3 has mark parts 5 provided at the four edges 3*a* of the microplate 1, not in only one edge as in the first embodiment. The mark parts 5 provided in the long edges 3*a* serve to identify the columns of wells. The mark parts 5 provided at the short edges 3*a* serve to identify the rows of wells. Thus, the mark parts 5 provided at the neighboring edges 3*a* can serve to identify the individual wells in the same way as in the first embodiment. In addition, two mark parts 5, one provided at one edge 3*a* and the other provided at the neighboring edge 3*a*, to identify the microplate 1. This method can identify the well in $2^{40}$ ways at most, because the base of the microplate 1 has 40 mark parts as shown in FIG. 3, twelve mark parts in either long edge and eight mark part in either short edge.

Figure 4:
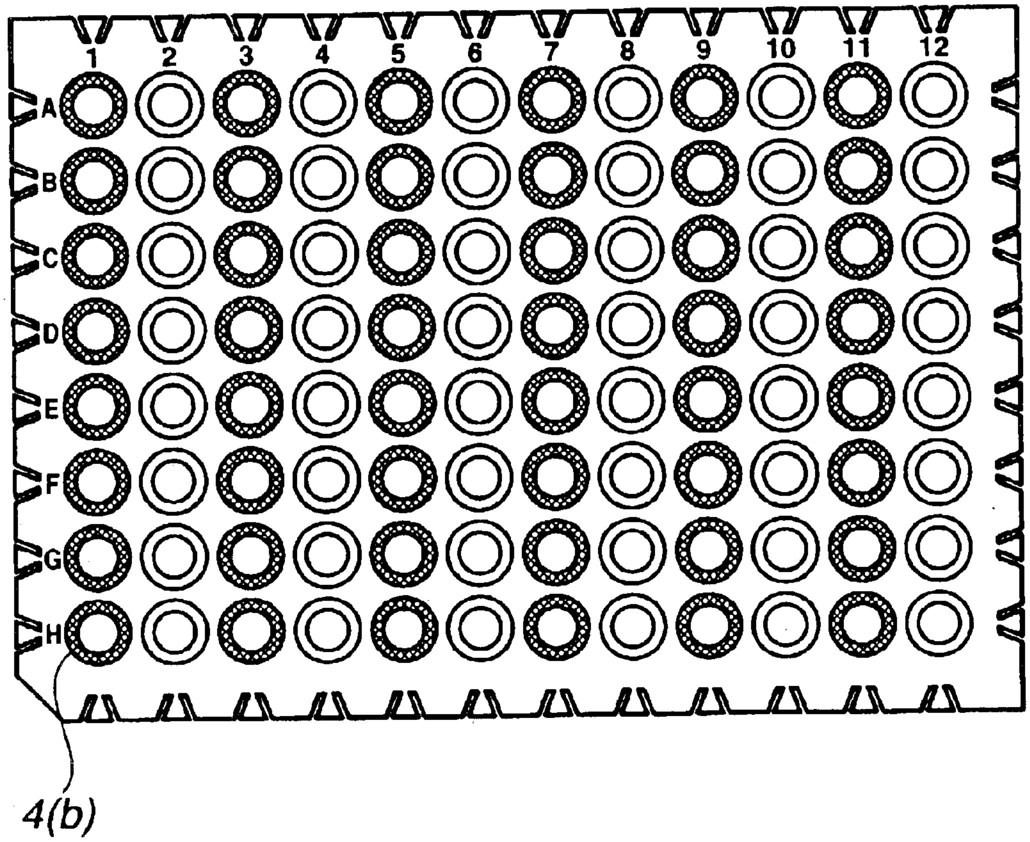
FIG. 4 is a top view of a microplate according to the third embodiment of the invention.

FIG. 4 depicts a microplate 1 according to the third embodiment of the invention. The third embodiment is identical to the second, except that the rims 4(*b*) of the wells 2 of every other column are different in color from the base 3. In most cases, microplates are either transparent or translucent. In some cases, microplates are colored. In the third embodiment, it does not matter whether the base 3 is colored or not and whichever color it has if colored. The third embodiment is characterized in that the rims 4(*b*) of the wells of every other column bear a color different from that of the base 3. As in the second embodiment, the mark parts 5 provided at the four edges 3*a* of the base 3 are used to identify the wells. The rims 4(*b*) thus colored helps people to distinguish the wells from those of the adjacent column. Hence, it is easier for people to identify the wells than with the second embodiment. The rims 4(*b*) may be colored by printing. However, the paint used may be dissolved into the liquid samples contained in the wells. In view of this it is desired that the rims 4(*b*) be formed integral with the base 3 and be made of a material that is identical to the material of the base 3 but different in color.

As explained above and as shown in FIG. 4, the rims of the wells of every other column are colored. Instead, the rims of the wells of every other row may be colored.

The present invention is not limited to the embodiments described above. For example, the arrangement of wells is not limited to the above-mentioned 8 row×12 column layout. Rather, the wells can be arranged in any number of rows and any number of columns as is desired. The wells may be arranged, for example, in three rows and three columns, thus forming a substantially square matrix of wells.

Figure 5A:
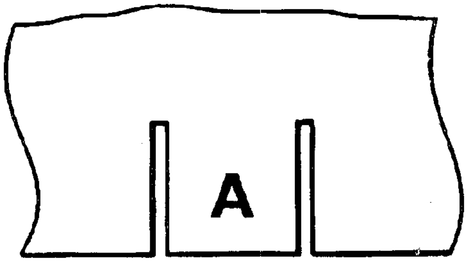
FIGS. 5A to 5E show various modifications of the mark.
Figure 5D:
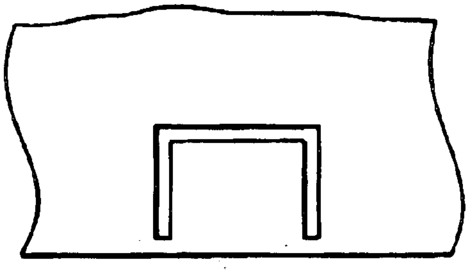
Figure 5B:
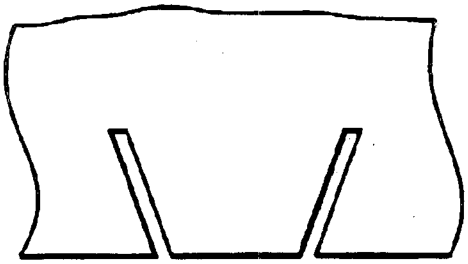
Figure 5E:
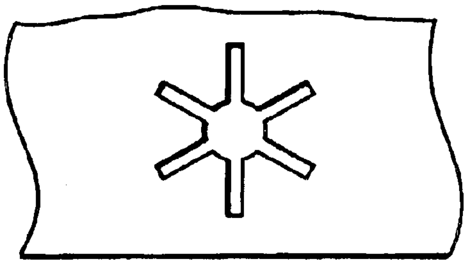
Figure 5C:
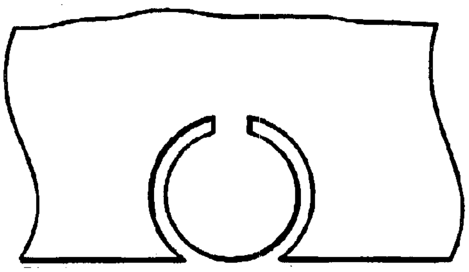

The shapes of the mark parts 5 is not limited to that applied in the first, second and third embodiments. The mark parts 5 can be modified in various ways. FIGS. 5A to 5E show some of the modified mark parts. The mark parts 5 of the embodiments described above have their width gradually decreasing toward the wells. Instead, the mark part shown in FIG. 5A has its width unchanged over its entire length. The mark part illustrated in FIG. 5B is shaped like an inverted trapezoid, with its width increasing toward the wells. The mark part depicted in FIG. 5C is circular, defined by two arced notches, and has a slender neck. The mark part shown in FIG. 5D is rectangular, defined by a channel-shaped slit cut in the base 3. The mark part depicted in FIG. 5E is defined by an impeller-shaped slit cut in the base 3 and has radial projections. In the case of the mark part shown in FIG. 5E, at least one radial projection may be pushed with the tip of a ball-point pen until the mark is deformed. Furthermore, a numeral, letter or symbol may be printed on each mark part as is illustrated in FIG. 5A.

As described above, the base 3 is a flat plate in the first, second and third embodiments. Alternatively, the base 3 may have side walls that project downwards from the four edges 3*a*. In this case, mark parts 5 can be provided in the side walls.

As has been described, the microplate according to the first embodiment of the present invention has mark parts provided at one or more edges of the base, which are used to identify the microplate. Hence, neither a serial number nor an ID mark needs to be written with a felt pen on the microplate to identify the microplate. (A serial number or an ID mark, if written, may be rubbed off, making it impossible to identify the microplate.) Formed integral with the microplate, the mark parts serves as three-dimensional indicia for the microplate. Even if many microplates are laid one upon another, the mark parts can be seen when the microplates are viewed sideways. This facilitates the identifying of each microplate.

The microplate according to the second embodiment of this invention has mark parts provided at the edges of the base, some of the mark parts aligned with the rows of wells and the remaining mark parts aligned with the columns of wells. The mark parts can therefore be used as indicia that serve to identify not only the microplate but also the respective wells. If any two mark parts are used, one provided at one edge and the other provided at the neighboring edge, the wells can be identified in $2^n$ ways at most, where n is the number mark parts provided.

The microplate according to the third embodiment of this invention has mark parts provided at the edges of the base, some of the mark parts aligned with the rows of wells and the remaining mark parts aligned with the columns of wells. Further, the rims of the wells of every other column are colored. Hence, people can visually identify the wells more easily than with the microplate according to the second embodiment.

Obviously, many modifications and variations of the present invention are possible in the light of the above teachings. It is therefore to be understood that within the scope of the appended claims, the invention may be practiced otherwise than as specifically described.

What is claimed is:

1. A microplate comprising:

a base having mark parts at least on one edge thereof, each mark part being defined by notches cut in said edge; and a plurality of wells provided in the base and arranged in rows and columns.

2. A microplate according to claim 1, wherein some of the mark parts are aligned with the rows of wells, respectively, and the remaining mark parts are aligned with the columns of wells, respectively.

3. A microplate according to claim 2, wherein each of the wells has a rim at the upper end, and the wells of every other row or every other column are different in color from the base.

* * * * *